United States Patent
Huang et al.

(10) Patent No.: US 11,229,605 B2
(45) Date of Patent: Jan. 25, 2022

(54) PRINTED SUPPORT STRUCTURE

(71) Applicant: HEWLETT-PACKARD DEVELOPMENT COMPANY, L.P., Houston, TX (US)

(72) Inventors: Wei Huang, Palo Alto, CA (US); Nathan Moroney, Palo Alto, CA (US); Steven J. Simske, Fort Collins, CO (US); Gary J. Dispoto, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 839 days.

(21) Appl. No.: 16/077,321

(22) PCT Filed: Feb. 15, 2017

(86) PCT No.: PCT/US2017/017992
§ 371 (c)(1),
(2) Date: Aug. 10, 2018

(87) PCT Pub. No.: WO2018/151725
PCT Pub. Date: Aug. 23, 2018

(65) Prior Publication Data
US 2021/0205228 A1    Jul. 8, 2021

(51) Int. Cl.
*A61K 9/20* (2006.01)
*B33Y 10/00* (2015.01)
*B33Y 80/00* (2015.01)
*B33Y 70/00* (2020.01)
*A61J 3/00* (2006.01)
*A61J 1/03* (2006.01)

(52) U.S. Cl.
CPC ............ *A61K 9/2072* (2013.01); *A61J 3/007* (2013.01); *A61K 9/2095* (2013.01); *B33Y 10/00* (2014.12); *B33Y 70/00* (2014.12); *B33Y 80/00* (2014.12); *A61J 1/035* (2013.01)

(58) Field of Classification Search
None
See application file for complete search history.

(56) References Cited

U.S. PATENT DOCUMENTS

| | | | |
|---|---|---|---|
| 7,931,914 B2 | 4/2011 | Pryce et al. | |
| 8,978,890 B2 | 3/2015 | Ludwig et al. | |
| 2006/0122729 A1 | 6/2006 | Murphy et al. | |
| 2006/0147493 A1* | 7/2006 | Yang | A61K 8/02 424/439 |
| 2008/0111282 A1 | 5/2008 | Xie et al. | |
| 2013/0193621 A1 | 8/2013 | Daya et al. | |
| 2015/0290280 A1 | 10/2015 | Petrak et al. | |
| 2016/0143810 A1 | 5/2016 | Stevens | |

FOREIGN PATENT DOCUMENTS

WO    2016170526 A1    10/2016

* cited by examiner

*Primary Examiner* — H. Sarah Park
(74) *Attorney, Agent, or Firm* — HP Inc. Patent Department

(57) ABSTRACT

An example device includes at least one three-dimensional (3D) printed tablet and a 3D-printed production support structure. Each 3D-printed tablet includes an excipient material and an active ingredient. The 3D-printed support structure includes a 3D-printed planar structure comprising the excipient material and at least one 3D-printed connecting member comprising the excipient material. The planar structure includes at least one aperture, each aperture corresponding to one of the at least one 3D-printed tablet. The connecting member detachably connects the at least one 3D-printed tablet with the 3D-printed planar structure and positions the at least one 3D-printed tablets within the apertures.

10 Claims, 6 Drawing Sheets

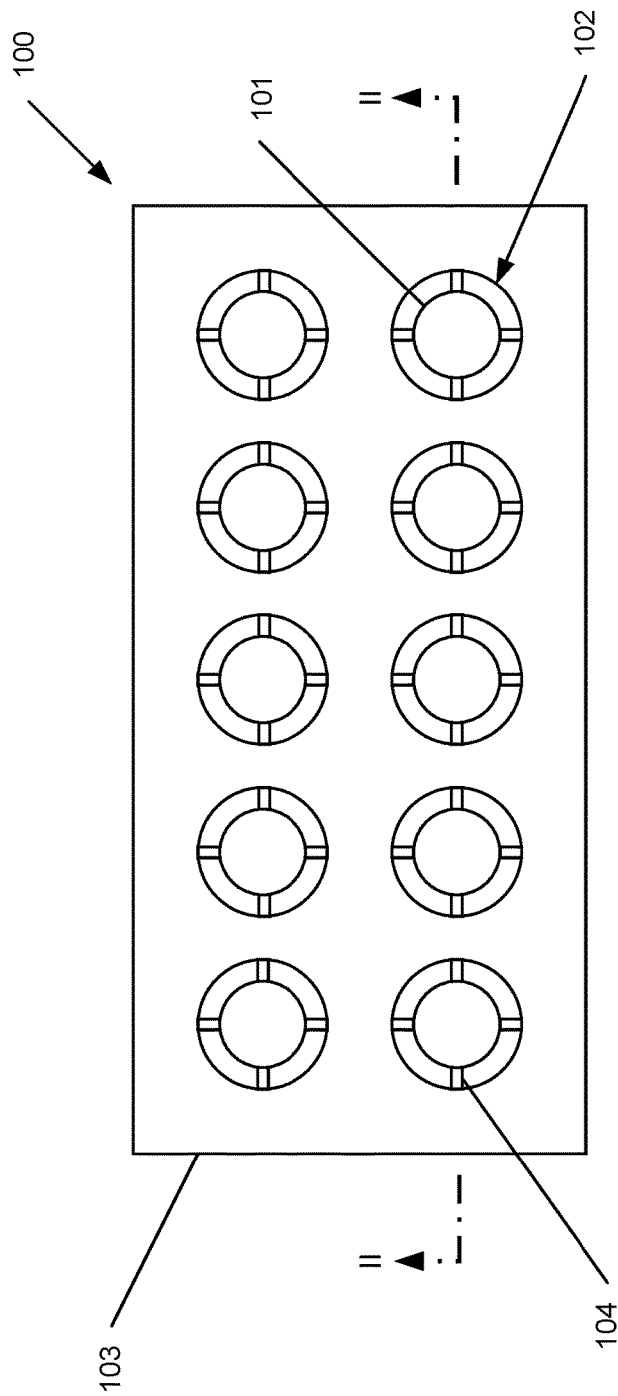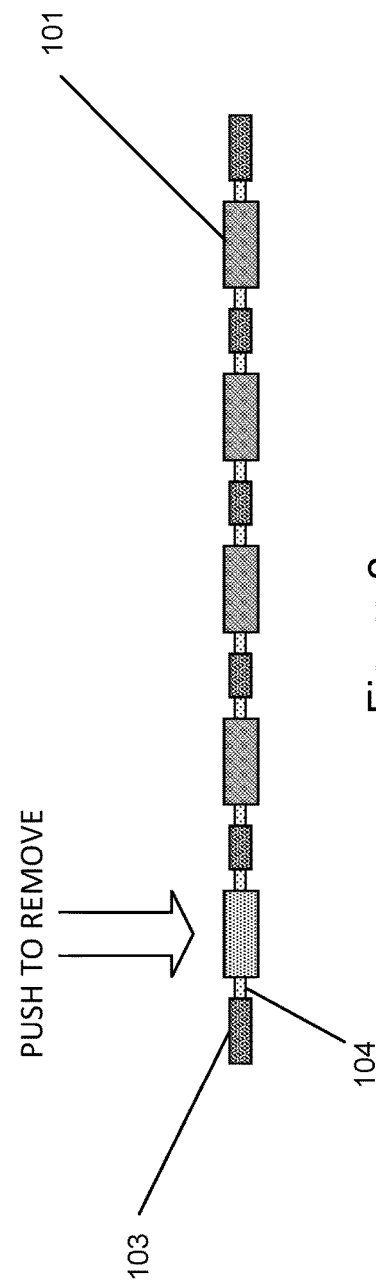

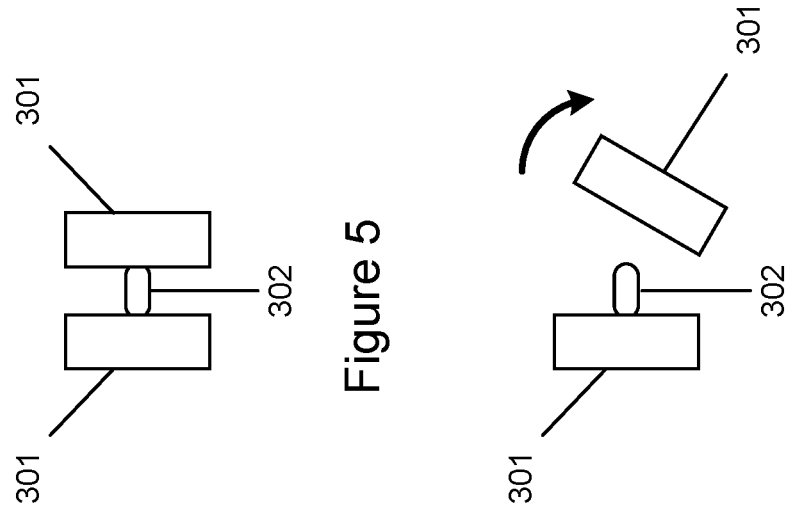
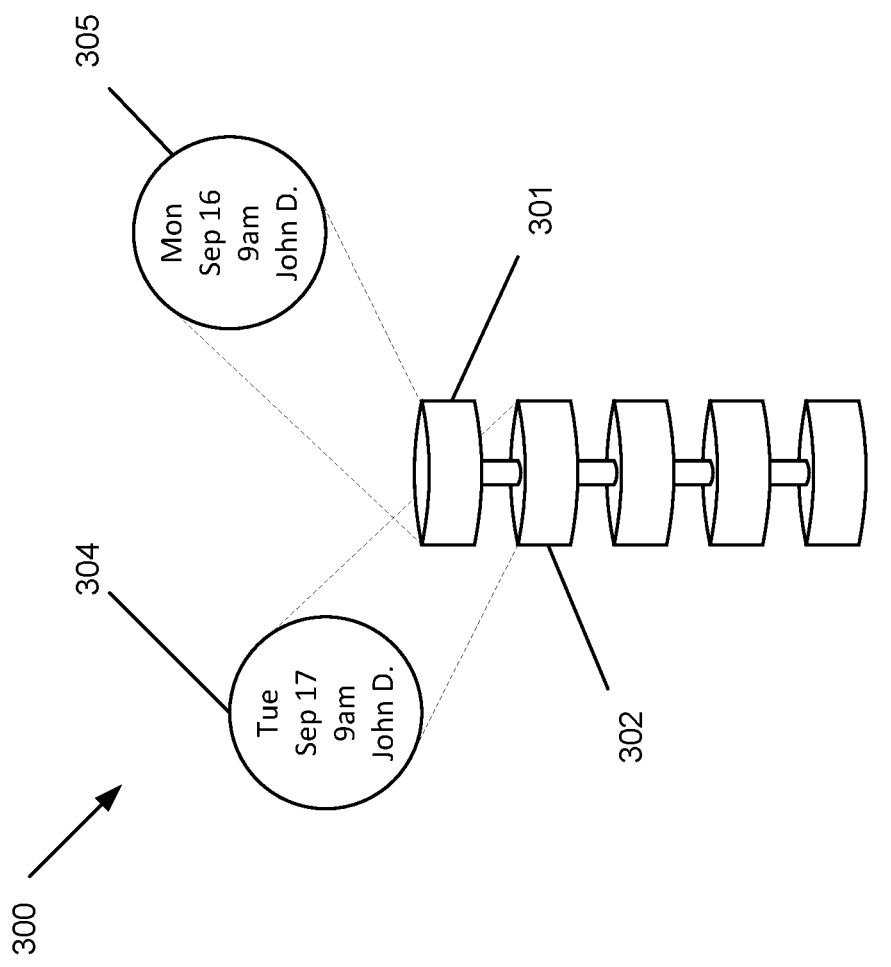

PRINTED SUPPORT STRUCTURE

BACKGROUND

Three-dimensional (3D) printing is becoming prevalent in a variety of applications. For example, 3D printing may be used to manufacture, or print, tablets of pharmaceutical products. In 3D printing of pharmaceuticals, tablets are formed individually from the source materials and the individual tablets are retrieved for subsequent post-processing, sorting and packaging.

BRIEF DESCRIPTION OF THE DRAWINGS

For a more complete understanding of various examples, reference is now made to the following description taken in connection with the accompanying drawings in which:

FIG. 1 is a top view of an example device for 3D-printed tablets with printed production support;

FIG. 2 is a cross-sectional view of the example device of FIG. 1 taken along II-II;

FIG. 4 is a perspective view of another example device for 3D-printed tablets with printed production support and printed information;

FIG. 5 is an example device for 3D-printed tablets joined by a 3D-printed connecting member;

FIG. 6 illustrates the separation of the example 3D-printed tablets in the example device of FIG. 5;

DETAILED DESCRIPTION

Figure 3:
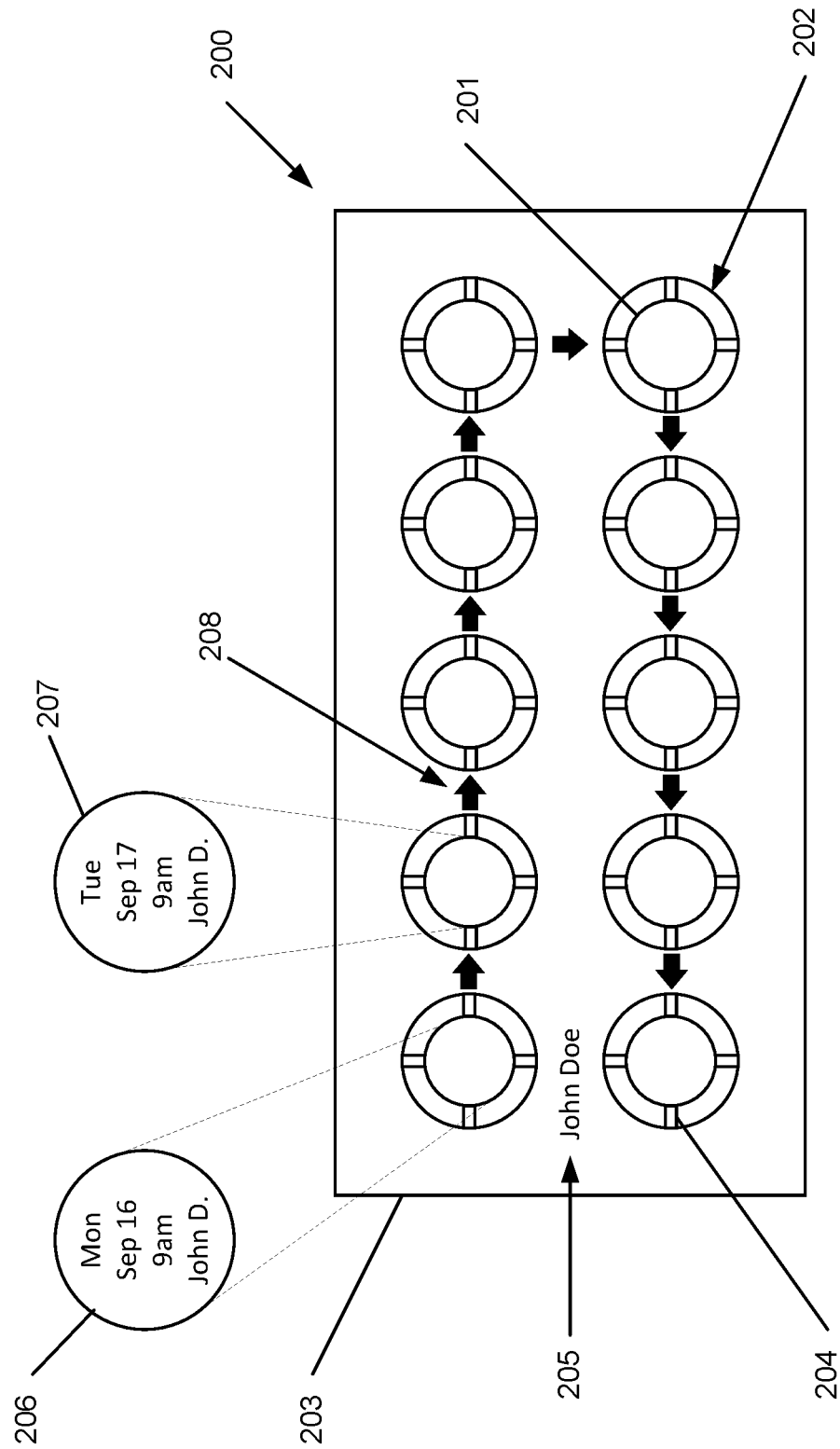
FIG. 3 is a top view of an example device for 3D-printed tablets with printed production support and packaging and printed information.

Various examples provide printed production supports for 3D-printed tablets to facilitate automated unpacking, cleaning and recycling operations, to provide components of final product packaging, and to provide printed information on the product for a consumer. In various examples, devices include 3D-printed tablets including an excipient material, or a carrier, and an active ingredient (e.g., a pharmaceutical or nutrient). In some examples, 3D-printed connecting members comprising the excipient material may detachably connect the 3D-printed tablets in a prescribed sequence and/or defined physical configuration such as, for example, a stack or planar array.

In some examples, the 3D-printed tablets may be supported by a production support structure. The production support structure may include a 3D-printed planar structure comprising the excipient material, with apertures corresponding to the 3D-printed tablets. The production support structure may also include 3D-printed connecting members, comprising the excipient material, to detachably connect the 3D-printed tablets with the 3D-printed planar structure and to position the 3D-printed tablets within the apertures in the 3D-printed planar structure.

The 3D-printed structures and 3D-printing processes described herein may be realized using any 3D-printing technology capable of printing two or more materials or compounds. Examples of such 3D-printing technologies include, without limitation, fused deposition modeling (FDM), selective laser sintering (SLS), 3D binder jetting, and multi jet fusion (MJF).

In 3D printing, a 3D structure is printed by forming successive layers of a material, such as by fusing of a powder. A 3D printer may base the forming of the layers on a computer-aided design (CAD) model or a 3D scan of an existing structure, for example. The thickness of each layer of the successive layers may vary from one printer to another. In this regard, smaller layers correspond to a higher resolution. In some examples, each layer may be formed by selectively fusing a layer of powder using energy from a laser, for example. 3D printers may be of any of a variety of sizes and resolutions, for example, to accommodate various types of applications.

In various examples, a 3D printer may implement a power-based fusing technique. In such examples, the 3D printer may include various components including, but not limited to, a recoater, a fusing device and a fusing agent delivery device. In other examples, the 3D printer may be a fused deposition modeling printer. In such cases, the printer may include an extrusion nozzle and a reservoir for holding the fusing material, for example.

Various structures may be formed by 3D printing processes by scanning various components of the 3D printer across a print bed. In various examples, a build material may be applied in layers. The build material may be particles of electrical non-conductive material in powder form. Various components of the 3D printer may be scanned across the layer of build material to selectively fuse the build material particles in certain areas of each layer to form the desired structure.

Referring now to the figures, FIGS. 1 and 2 illustrate, respectively, top and sectional views of an example device 100 of a planar array of 3D-printed tablets 101 positioned within a corresponding number of apertures 102 of a 3D-printed planar support structure 103. The example device 100 of FIG. 1 is illustrated with ten tablets, but various examples may be provided with any number of tablets as desired. The 3D-printed tablets 101 are connected to the planar support structure by 3D-printed connecting members 104, which secure and position the 3D-printed tablets within the apertures 102.

The arrangement of the tablets 101 within the support structure 103 can be standardized to enable automated post-printing processing operations such as unpacking, cleaning and recycling (UCR) operations and conveying operations that would be difficult to perform on small, loose, individual tablets. While FIG. 1 illustrates a rectangular array of 3D printed tablets 101 as an example, it will be appreciated that other configurations are possible and contemplated within the scope of the present disclosure. For example, a single linear array, a circular array, or any other geometric configuration with regularity or periodicity that is amenable to modeling in an automated machine environment is possible. In one example, after any post-printing processing is completed, the 3D-printed tablets 101 may be removed from the production support structure 103 by applying pressure to the tablets 101, normal to the plane of the support structure 103 as illustrated in FIG. 2. Upon removal from the support structure 103, the tablets 101 may be collected for final packaging operations, such as blister packaging.

As noted above, the 3D-printed tablets 101 may be printed using both an excipient material and an active ingredient, such as a pharmaceutical or a nutritional agent (e.g., vitamins and minerals). Depending on the 3D printing technology being used, there may be more than one active ingredient. For example, in the case of multi jet fusion (MJF) printing with multiple inkjet nozzles, the number of active ingredients would be limited only by the number of nozzles.

The excipient material may be, for example, one or more edible polymers or digestible organic compounds. In various examples, the excipient material may be a single compound or a uniform mixture of compounds. In some examples, the excipient material may be provided as a powder bed or as a liquid reservoir, where the material can be fused or solidified, respectively, using an energy source such as a thermal, laser or other photo-optical energy source, or any other energy source appropriate for the particular type of excipient material being used. In some examples, the material may be left unfused or partially fused. In other examples, the excipient material may be provided as a component of an ink from an inkjet nozzle in the example of MJF printing.

In various examples, different portions of the printed volume may be treated differently from a thermal perspective. For example, an internal portion of a tablet may be left unfused while an outer shell may be fused. In this regard, the internal portion may not be subjected to potentially harmful heat, which may in some cases lead to unwanted chemical changes.

Because 3D printing relies on the printing of multiple thin layers, and the energy used to fuse or solidify the excipient material(s) is a controllable variable, the structure of the tablets can be customized to achieve desired effects, such as in-vivo release control, where the tablets are designed to be physically or chemically depleted, either completely or partially, for controlled release of the active ingredient(s) carried by the excipient materials, whether by degradation, dissolution, diffusion, sublimation or any other physical or chemical depleting process. Control over the level of fusing in the excipient material may be used to determine the density and porosity of the excipient material, which may be used to control the amount of active ingredient in each tablet. Additionally, in some examples using multiple excipient materials, different excipient materials may be printed in different layers or groups of layers to achieve different controlled release profiles.

During the layered printing of the tablets 101, controlled amounts of the active ingredient(s) may be deposited concurrently with the excipient material in each tablet 101, forming an internal component of each tablet 101 to achieve a desired total dosage and dosage profile determined by the depletion rate of the excipient material. In some examples, the active ingredient(s) may be formulated as part of a printed ink, which may solidify within each tablet or remain in liquid form within each tablet.

The connecting members 104 may be fabricated from the excipient material in at least two ways to achieve easy removal of the tablets 101 from the planar support structure 103. In one example, the connecting members 104 may be printed as fully fused components with a thinner cross-section relative to the thickness of the planar support structure 103 as illustrated in FIG. 2. In another example (not shown), the connecting members 104 may be printed as semi-fused components with a thinner cross-section relative to the thickness of the planar support structure 103. In either example, the resulting connecting members 104 will be relatively weaker than the surrounding planar support structure 103, facilitating removal of the tablets 101. While FIG. 1 illustrates the use of 4 connecting members 104 attaching each tablet 101 to the planar support structure 103, it will be appreciated that other configurations are possible, including without limitation, configurations with two connecting members per tablet 101, or three connecting members 104 per tablet 101.

Turning now to FIG. 3, there is illustrated a top view of an example device 200 for 3D-printed tablets with 3D-printed production support and packaging components, and with additional printed information. In the example of FIG. 3, 3D-printed tablets 201, 3D-printed planar support structure 203 and 3D-printed connecting members 204 may be similar to the corresponding elements 101, 103 and 104 of FIGS. 1 and 2, as described above with respect to structure and fabrication, which details are not repeated here. It will be appreciated that the example illustrated in FIG. 3 may accordingly have similar properties with respect to controlled release, dosage profiles and post-printing UCR operations.

In the example of FIG. 3, there is illustrated additional printed information. As described below, such printed information in combination with customized 3D-printed pharmaceutical or nutrition tablets may be used to provide patient customized dosage sequence, dosage timing and dosage profile.

In one example, a patient may receive a medical prescription that defines when each dose is to be taken with respect to date and time of day, a total dose delivered by each tablet, and even a customized release profile for each tablet. That prescription may then be transmitted to a local or centralized 3D printing pharmaceutical facility for fulfillment. It will be appreciated from the foregoing disclosure of 3D printing of pharmaceuticals, that such customization is well within the boundaries of the disclosed technology, and that tablets conforming to the prescription may be fabricated within a production support structure as previously described. In the example illustrated in FIG. 3, rather than removing the 3D-printed tablets 201 from the 3D-printed planar support structure 203 after post-printing UCR operations, the 3D-printed tablets 201 may remain attached to the 3D-printed planar support structure 203, which may be used as a component of final packaging for delivery of the prescription to the patient. For example, the entire 3D-printed structure 200 could be placed in a blister pack, in a cardboard container or covered with plastic shrink wrap.

As illustrated in the example of FIG. 3, additional printed information may include the patient name 205 (e.g., John Doe) and labels such as, for example, typical labels 206 and 207 and typical arrows or other indicia that may indicate a prescribed sequence, such as the day, date and the time of day that the pharmaceutical should be taken, as well as the name of the patient to ensure that the medication is taken by the right person. In one example, the ink used for the printed information may include the active ingredient(s) as a component.

In some examples, the connecting members 104, 204 are printed with a thickness approximately equal to a thickness of the planar support structure 103, 203 and with a density less than a density of the support structure 103, 203. In other examples, the connecting members 104, 204 are printed with a thickness less than a thickness of the support structure 103, 203 and with a density approximately equal to a density of the support structure 103, 203.

Turning now to FIG. 4, there is illustrated an example device 300 for 3D-printed tablets with printed production support and printed information. FIG. 4 includes 3D-printed tablets 301 comprising an excipient material and an active ingredient as previously described. The 3D-printed tablets 301 may be connected to each other by 3D-printed connecting members 302 to form a stack of 3D-printed tablets 301.

The 3D-connecting members 302 may be similar in all respects to the 3D-connecting members 104 and 204 described in detail above, and provide detachable connections between the 3D-printed tablets 301. In one example, and as described above, additional printed information may include labels on the 3D-printed tablets such as, for example, labels 303 and 304 describing a prescribed sequence for consuming the medication, such as day, date and time of day for example. In one example, the ink used to print the labels 303 and 304 may include an active ingredient as a component. It will be appreciated that the 3D-printed tablets 301 in the configuration illustrated in FIG. 4 could be placed in a final package for delivery to a consumer. Examples of such packaging may include a tube with a twist-off cap, a plastic shrink wrapping or the like.

FIGS. 5 and 6 illustrate an example operation of the detachable connections provided by the connecting members 302. FIG. 5 illustrates an example of two 3D-printed tablets connected by a 3D-printed connecting member 302 in an as-printed configuration. FIG. 6 illustrates an example of a bend-to-break operation used to separate the 3D-printed tablets 301.

Figure 7:
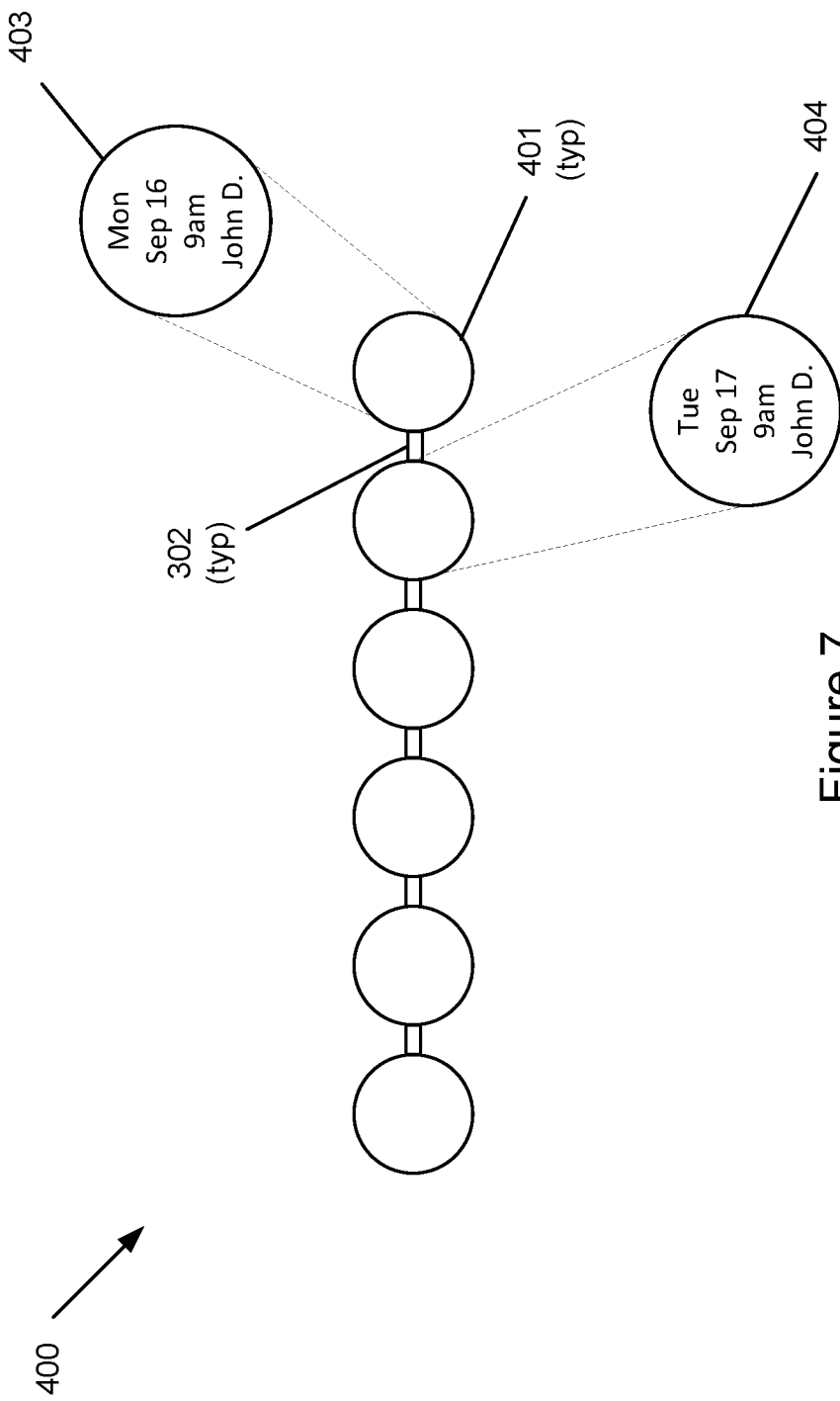
FIG. 7 is a top view of another example device for 3D-printed tablets with production support.

FIG. 7 illustrates an example device 400 for 3D-printed tablets with printed production support and printed information. FIG. 7 includes 3D-printed tablets 401 comprising an excipient material and an active ingredient as previously described. The 3D-printed tablets 401 may be connected to each other by 3D-printed connecting members 402 to form a linear array of 3D-printed tablets 401. The 3D-printed connecting members 402 may be similar in all respects to the 3D-printed connecting members 104 and 204 described in detail above, and provide detachable connections between the 3D-printed tablets 401. In one example, and as described above, additional printed information may include labels on the 3D-printed tablets such as, for example, labels 403 and 404 describing a prescribed sequence for consuming the medication, such as day, date and time of day for example. In one example, the ink used to print the example labels 403 and 404 may include an active ingredient as a component. It will be appreciated that the 3D-printed tablets 401 in the configuration illustrated in FIG. 4 could be placed in a final package for delivery to a consumer as described above.

Figure 8:
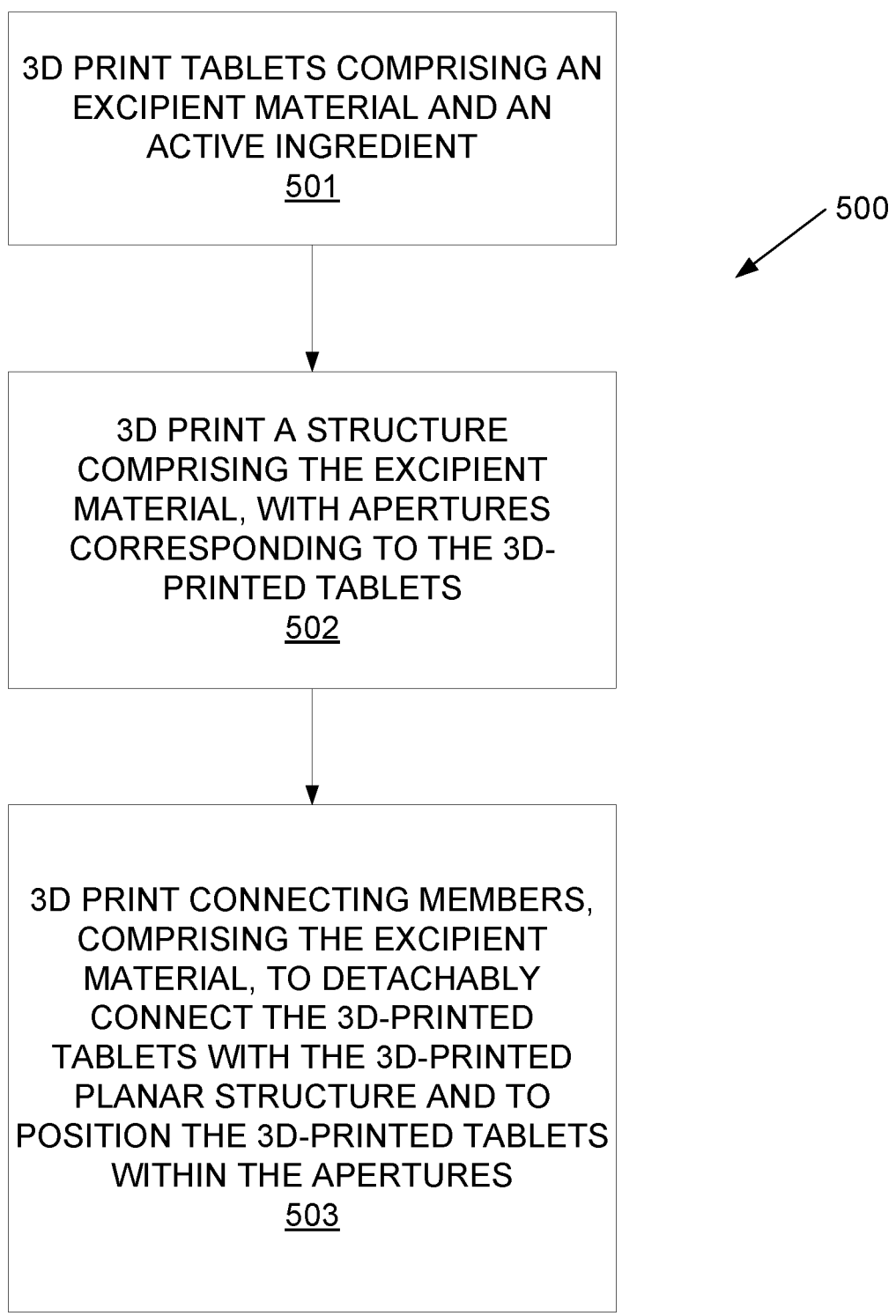
FIG. 8 is a flowchart illustrating an example process for manufacturing 3D-printed tablets with production support.

FIG. 8 is a flowchart for an example process 500 for manufacturing 3D-printed tablets with production support and packaging, such as the example 3D-printed structure 200 illustrated in FIG. 3. The example process 500 begins with operation 501, 3D printing tablets (e.g., 201) comprising an excipient material and an active ingredient. The example process 500 continues at operation 502, 3D printing a planar structure (e.g., 203) comprising the excipient material, with apertures (e.g., 202) corresponding to the 3D-printed tablets. The example process 500 then continues at operation 503, 3D printing connecting members (e.g., 204), comprising the excipient material, to detachably connect 3D-printed tablets with the 3D-printed planar structure and to position the 3D-printed tablets within the apertures.

Figure 9:
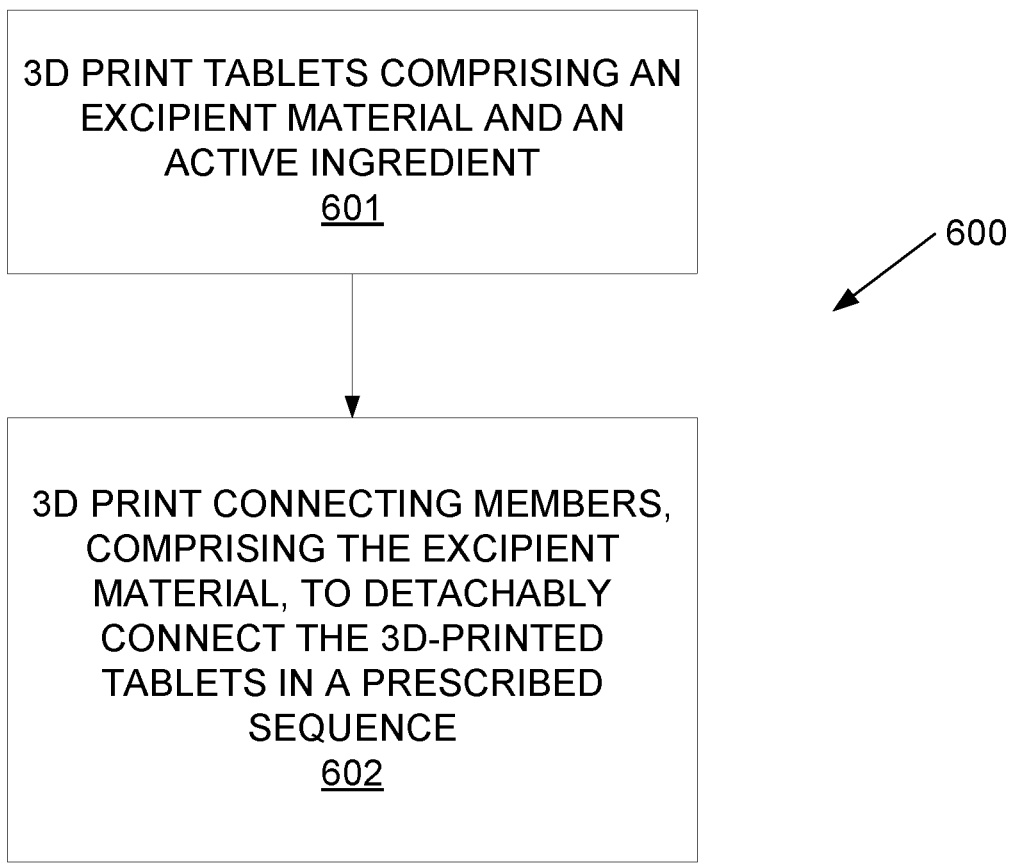
FIG. 9 is a flowchart illustrating an example process for manufacturing 3D-printed tablets with production support.

FIG. 9 is a flowchart for an example process 600 for manufacturing 3D-printed tablets with production support, such as the example 3D-printed structure 300 illustrated in FIG. 4 and the example 3D-printed structure 400 illustrated in FIG. 7. The example process 600 begins with operation 601, 3D printing tablets (e.g., 301, 401) comprising an excipient material and an active ingredient. The example process 600 continues at operation 602, 3D printing connecting members (e.g., 302, 402), comprising the excipient material, to detachably connect the 3D-printed tablets in a prescribed sequence.

With respect to the example process 500 and the example process 600, it will be appreciated that due to the nature of 3D printing, in some examples, the example process 500 may be viewed as an iterative process with many passes corresponding to individual layers as they are printed. It will also be appreciated that not every component of the corresponding 3D-printed structure will be present in every layer so that some operations may be omitted in some layers. It will also be appreciated that the order of operations in the processes may be altered in the printing of any given layer.

Thus, in accordance with various examples described herein, 3D-printed tablets may be fabricated with integral production support and packaging.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. A device, comprising:
   at least one three-dimensional (3D) printed tablet, each 3D-printed tablet comprising an excipient material and an active ingredient; and
   a 3D-printed production support structure, the 3D-printed support structure comprising:
   a 3D-printed planar structure comprising the excipient material, the planar structure including at least one aperture, each aperture corresponding to one of the at least one 3D-printed tablet; and
   at least one 3D-printed connecting member comprising the excipient material, the connecting member detachably connecting the at least one 3D-printed tablet with the 3D-printed planar structure and positioning the at least one 3D-printed tablet within the aperture.

2. The device of claim 1, wherein the active ingredient comprises a printed ink on the 3D-printed tablets.

3. The device of claim 2, wherein the printed ink indicates a prescribed dosage sequence.

4. The device of claim 1, wherein the excipient material of the 3D-printed tablets is a porous substrate, and wherein the active ingredient is 3D-printed within the porous substrate.

5. The device of claim 1, wherein the excipient material comprises one of an organic compound and an edible inorganic polymer.

6. A method, comprising:
   three-dimensional (3D) printing tablets comprising an excipient material and an active ingredient; and
   3D printing a production support structure, the production support structure comprising:

a 3D printed planar structure comprising the excipient material, the planar structure including apertures corresponding to each of the 3D printed tablets; and at least one 3D printed connecting member comprising the excipient material, the connecting member detachably connecting the 3D-printed tablets with the 3D-printed planar structure and positioning the 3D-printed tablets within the apertures.

7. The method of claim 6, wherein the connecting members are printed with a thickness approximately equal to a thickness of the planar structure and with a density less than a density of the planar structure.

8. The method of claim 6, wherein the connecting members are printed with a thickness less than a thickness of the planar structure and with a density approximately equal to a density of the planar structure.

9. The method of claim 6, wherein the active ingredient is 3D-printed as an internal component of the 3D-printed tablets.

10. The method of claim 6, wherein the active ingredient is 3D-printed as labels on the 3D-printed tablets indicating a prescribed sequence.

\* \* \* \* \*